(12) United States Patent
Cho et al.

(10) Patent No.: US 10,548,404 B2
(45) Date of Patent: Feb. 4, 2020

(54) PRESSURE SENSING CHAIR

(71) Applicant: LG INNOTEK CO., LTD., Seoul (KR)

(72) Inventors: Won Keun Cho, Seoul (KR); Bi Yi Kim, Seoul (KR); Jeong Han Kim, Seoul (KR); Hyun Gyu Park, Seoul (KR); In Hee Cho, Seoul (KR); Hyun Jin Jo, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 0 days.

(21) Appl. No.: 15/757,494

(22) PCT Filed: Sep. 2, 2016

(86) PCT No.: PCT/KR2016/009878
§ 371 (c)(1),
(2) Date: Mar. 5, 2018

(87) PCT Pub. No.: WO2017/039403
PCT Pub. Date: Mar. 9, 2017

(65) Prior Publication Data
US 2019/0021504 A1    Jan. 24, 2019

(30) Foreign Application Priority Data

Sep. 3, 2015 (KR) .................. 10-2015-0125078

(51) Int. Cl.
*G01L 1/00* (2006.01)
*A47C 7/62* (2006.01)
(Continued)

(52) U.S. Cl.
CPC .............. *A47C 7/62* (2013.01); *A47B 21/06* (2013.01); *A47B 83/02* (2013.01); *G01L 1/14* (2013.01);
(Continued)

(58) Field of Classification Search
CPC .. A47C 7/62; A47C 7/00; A47B 21/06; A47B 83/02; A47B 2021/066;
(Continued)

(56) References Cited

U.S. PATENT DOCUMENTS 9,030,313 B1 * 5/2015 Pearson ................... B60N 2/26
180/273
2006/0261672 A1 * 11/2006 Richter ............... B60R 25/2027
307/10.1
(Continued)

FOREIGN PATENT DOCUMENTS

| JP | S62-250390 | 10/1987 |
|---|---|---|
| JP | 2014-119306 | 6/2014 |
| JP | 2015-089128 | 5/2015 |
| KR | 10-2010-0104946 | 9/2010 |
| KR | 10-2011-0008611 | 1/2011 |

OTHER PUBLICATIONS

International Search Report (with English Translation) and Written Opinion dated Dec. 8, 2016 issued in Application No. PCT/KR2016/009878.

*Primary Examiner* — Max H Noori
(74) *Attorney, Agent, or Firm* — KED & Associates LLP

(57) ABSTRACT

The present invention relates to a pressure sensing chair capable of wireless charging, detecting body pressure, and measuring the distribution of body pressure. A pressure sensing chair according to one embodiment of the present invention comprises: at least one sensor unit including a first electrode layer having a plurality of first electrode patterns arranged in a first direction, a second electrode layer having a plurality of second electrode patterns arranged in a second direction crossing the first direction, and a dielectric layer arranged between the first electrode layer and the second electrode layer; and a module unit connected to the sensor unit and including a communication unit and a wireless charging unit.

18 Claims, 6 Drawing Sheets

(51) Int. Cl.
    *G01L 1/14*      (2006.01)
    *A47B 21/06*     (2006.01)
    *A47B 83/02*     (2006.01)
    *H02J 50/10*     (2016.01)
    *H02J 7/02*      (2016.01)

(52) U.S. Cl.
    CPC ......... *A47B 2021/066* (2013.01); *H02J 7/025* (2013.01); *H02J 50/10* (2016.02)

(58) Field of Classification Search
    CPC ... A61B 5/103; G01L 1/14; G01L 5/00; H02J 7/025; H02J 50/10
    USPC .......................................................... 73/780
    See application file for complete search history.

(56) References Cited

U.S. PATENT DOCUMENTS

| | | | |
|---|---|---|---|
| 2007/0257821 A1* | 11/2007 | Son | G06F 3/016 341/22 |
| 2014/0085070 A1* | 3/2014 | Schoenberg | B60R 22/48 340/457.1 |
| 2015/0002447 A1* | 1/2015 | Schediwy | G06F 1/1692 345/174 |
| 2015/0102773 A1* | 4/2015 | Song | H02J 7/0042 320/108 |
| 2015/0196209 A1* | 7/2015 | Morris | G16H 40/67 600/480 |
| 2015/0380978 A1* | 12/2015 | Toivola | H02J 7/04 320/108 |
| 2018/0065504 A1* | 3/2018 | Lan | B60N 2/002 |

* cited by examiner

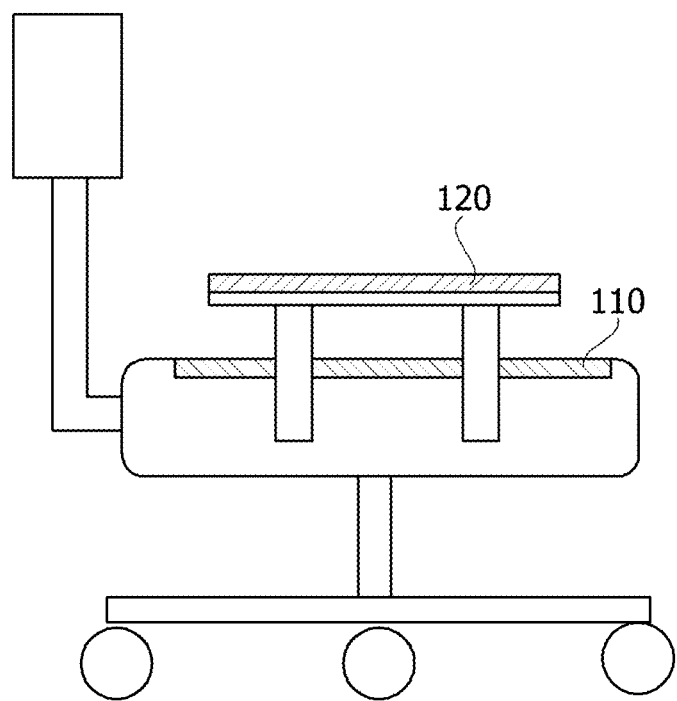

PRESSURE SENSING CHAIR

CROSS-REFERENCE TO RELATED PATENT APPLICATIONS

This application is a U.S. National Stage Application under 35 U.S.C. § 371 of PCT Application No. PCT/KR2016/009878, filed Sep.2,2016, which claims priority to Korean Patent Application No. 10-2015-0125078, filed Sep. 3, 2015, whose entire disclosures are hereby incorporated by reference.

TECHNICAL FIELD

The present invention relates to a pressure sensing chair, and more particularly, to a pressure sensing chair capable of wireless charging, sensing a body pressure, and measuring a distribution of the body pressure.

BACKGROUND ART

Recently, rapid development of electronic technology and information and communication technology has led to rapid development of health care fields. That is, a health management system capable of measuring body conditions of a person by measuring biometric information is required, and, specifically, techniques for obtaining biometric information using chairs mainly used in daily life are being developed.

However, in a conventional chair for obtaining biometric information, a plurality of independent sensors are required for measuring a facing area, and a space for connecting modules for driving each of the sensors is additionally required. Furthermore, since the sensor is not flexible and elastic, the sensor is difficult to be applied to a chair having a multiple curved surface.

DISCLOSURE

Technical Problem

The present invention is directed to providing a pressure sensing chair including a pressure sensing unit having flexibility and elasticity, and capable of wireless charging.

Technical Solution

One aspect of the present invention provides a pressure sensing chair including a sensor unit, and a module unit electrically connected to the sensor unit and including a communication unit and a wireless charging unit, wherein the sensor unit includes a first electrode layer including a plurality of first electrode patterns arranged in a first direction, a second electrode layer including a plurality of second electrode patterns arranged in a second direction crossing the first direction, and a dielectric layer arranged between the first electrode layer and the second electrode layer The sensor unit may sense a change in a thickness of the dielectric layer in regions which overlap the first electrode patterns and the second electrode patterns by an external pressure.

The communication unit may include a communication module such as a Bluetooth module, a Z-Wave module, or the like, and transmit pressure information sensed by the sensor unit to a receiver.

The wireless charging unit may receive wirelessly power using an electromagnetic induction method or a resonance method.

The first electrode layer and the second electrode layer may include fibers having conductivity or may be formed by printing a conductive ink on the dielectric layer.

The sensor unit may be disposed in at least one of a seat and a backrest.

The module unit may be disposed in an armrest.

The first electrode patterns and the second electrode patterns may have a shape selected from a bar shape, a zigzag shape, and a wavy shape.

Widths of the plurality of first electrode patterns may be the same as widths of the plurality of second electrode patterns.

At least some of the plurality of first electrode patterns and the plurality of second electrode patterns may have different widths.

The module unit may further include an alarm unit configured to output a signal of a posture correction.

Advantageous Effects

A pressure sensing chair according to an embodiment of the present invention has the following effects.

First, a sensor unit capable of detecting a pressure can be disposed in at least one of a seat and a backrest, so that a pressure distribution and posture information according to seating of a person can be sensed. Particularly, since the sensor unit is formed in the form of a mat, a facing area can be sensed.

Second, first and second electrode layers of the sensor unit can be formed of conductive fibers or can be formed by printing a conductive ink on a dielectric layer, and thus flexibility and elasticity of the sensor unit can be improved.

Third, since the pressure sensing chair includes a wireless charging unit, the pressure sensing chair can be wirelessly charged, and an on/off operation of the wireless charging unit can be controlled according to whether a pressure is sensed by the sensor unit.

Fourth, since the pressure sensing chair includes a communication unit, the pressure distribution and the posture information sensed by the sensor unit can be transmitted to an external device.

DESCRIPTION OF DRAWINGS

FIG. 1 is a side view of a pressure sensing chair according to an embodiment of the present invention.

MODES OF THE INVENTION

Figure 2A:
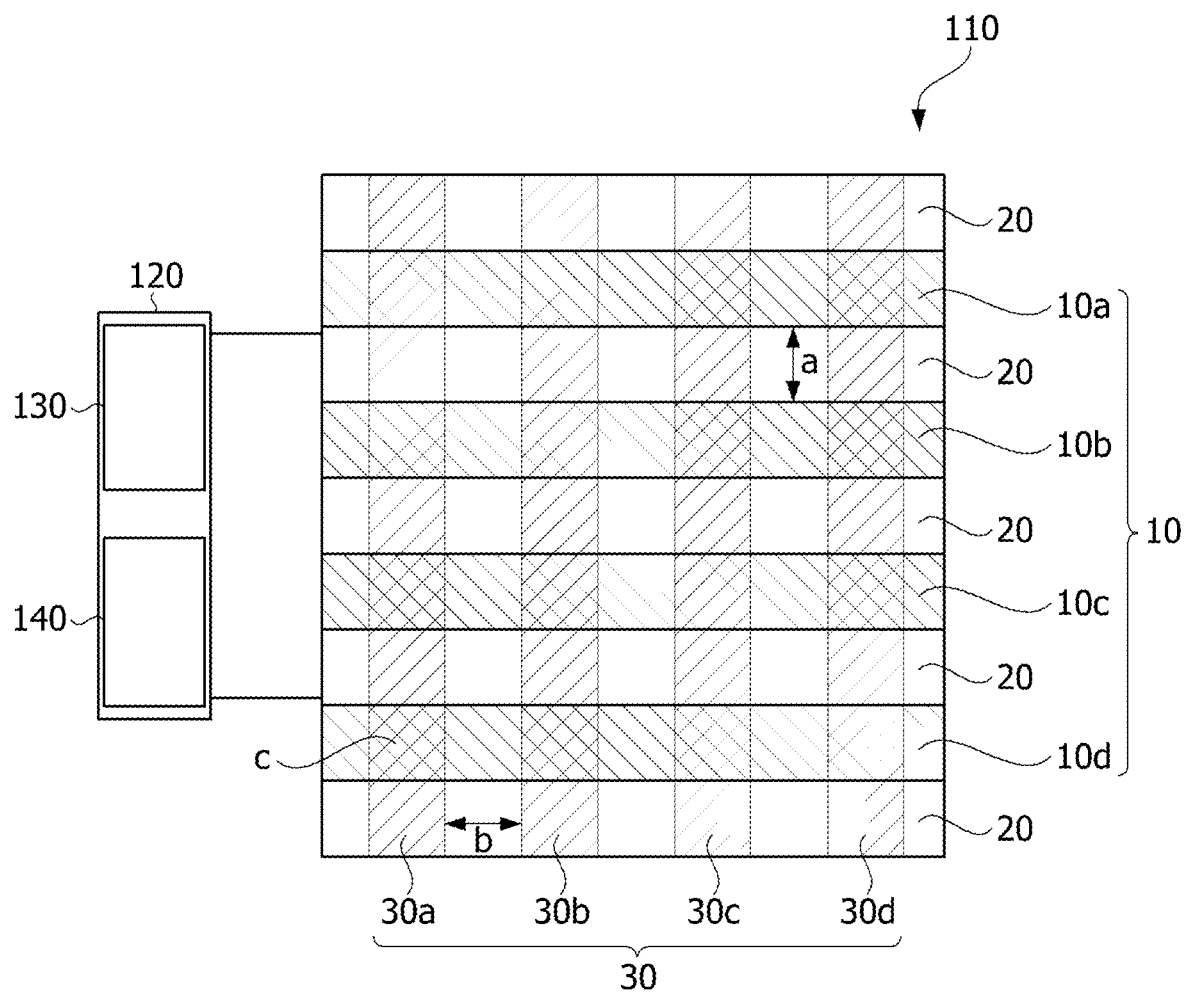
FIG. 2A is a plan view of FIG. 1.

While the present invention is susceptible to various modifications and alternative forms, specific embodiments thereof are shown by way of example in the drawings and will herein be described. It should be understood, however, that there is no intent to limit the present invention to the particular forms disclosed, but on the contrary, the present invention is to cover all modifications, equivalents, and alternatives falling within the spirit and scope of the present invention.

It will be understood that, although the terms "first," "second," etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It should be understood that when an element is referred to as being "connected" or "coupled" to another element, it can be directly connected or coupled to the other element or intervening elements may be present. In contrast, it should be understood that when an element is referred to as being "directly connected" or "directly coupled" to another element, there are no intervening elements present.

The terminology used herein is for the purpose of describing particular embodiments only and is not intended to be limiting of the present invention. As used herein, the singular forms "a," and "an" are intended to include the plural forms as well, unless the context clearly indicates otherwise. It should be further understood that the terms "comprise," "comprising," "include," and/or "including," when used herein, specify the presence of stated features, integers, steps, operations, elements, parts, or combination thereof, but do not preclude the presence or addition of one or more other features, integers, steps, operations, elements, parts, or combination thereof.

Unless otherwise defined, all terms (including technical and scientific terms) used herein have the same meaning as commonly understood by one of ordinary skill in the art to which this invention belongs. It should be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, exemplary embodiments of the present invention will be described in detail with reference to the accompanying drawings. In order to facilitate overall understanding of the present invention, like reference numerals in the drawings denote like elements, and thus the description thereof will not be repeated.

Hereinafter, a pressure sensing chair according to an embodiment of the present invention will be described in detail with reference to the accompanying drawings.

Figure 2B:
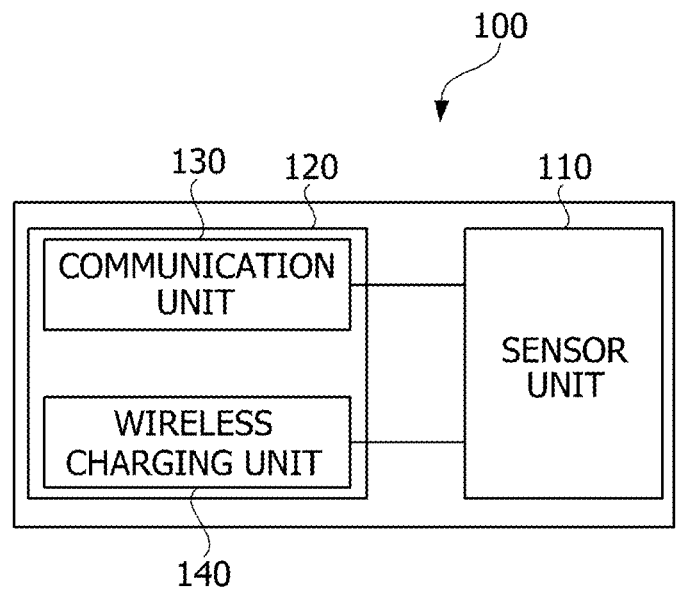
FIG. 2B is a block diagram of FIG. 2A.

FIG. 1 is a side view of the pressure sensing chair according to the embodiment of the present invention. FIG. 2A is a plan view of FIG. 1, and FIG. 2B is a block diagram of FIG. 2A.

As shown in FIG. 1, the pressure sensing chair according to the embodiment of the present invention may include a seat, a backrest, and an armrest, a sensor unit 110 may be disposed in the seat, and a module unit 120 may be disposed in the armrest. Specifically, the sensor unit 110 may be disposed on an upper surface of the seat or inside the seat.

When a person is seated on the above pressure sensing chair, the sensor unit 110 may be affected by a weight of the person, and may measure whether the person is seated thereon and a relative pressure distribution according to the seating. The module unit 120 may detect a posture of the person based on a body pressure detected by the sensor unit 110, and determine a pressure deviation of both thighs to guide the person to sit in a correct posture. Further, although not shown, the module unit 120 may further include an alarm unit (not shown) for outputting a signal of a posture correction to the person sitting on the chair.

Specifically, an on/off operation of the module unit 120 may be controlled according to whether the pressure is sensed by the sensor unit 110. That is, when the pressure is sensed by the sensor unit 110, the module unit 120 may be turned on, and when the pressure is not sensed by the sensor unit 110, the module unit 120 may be automatically turned off.

As shown in FIGS. 2A and 2B, the sensor unit 110 and the module unit 120 may be electrically connected, and the module unit 120 may include a communication unit 130 and a wireless charging unit 140. The sensor unit 110 is formed in the form of a mat and includes a dielectric layer 20, a first electrode layer 10, and a second electrode layer 30.

Here, the first electrode layer 10 includes a plurality of first electrode patterns 10a, 10b, 10c, and 10d which are arranged on a first surface of the dielectric layer 20 in a first direction. The second electrode layer 30 includes a plurality of second electrode patterns 30a, 30b, 30c, and 30d which are arranged on a second surface of the dielectric layer 20 opposite the first surface in a second direction crossing the first direction.

The communication unit 130 may include a communication module such as a Bluetooth module, a Z-Wave module, or the like, and transmit pressure information sensed by the sensor unit 110 to an external device, which is a receiver such as a smart phone, a computer, or the like. The wireless charging unit 140 may be electrically connected to a power source (not shown) of the sensor unit 110.

Hereinafter, the sensor unit 110 will be described in detail with reference to the accompanying drawings.

Figure 3:
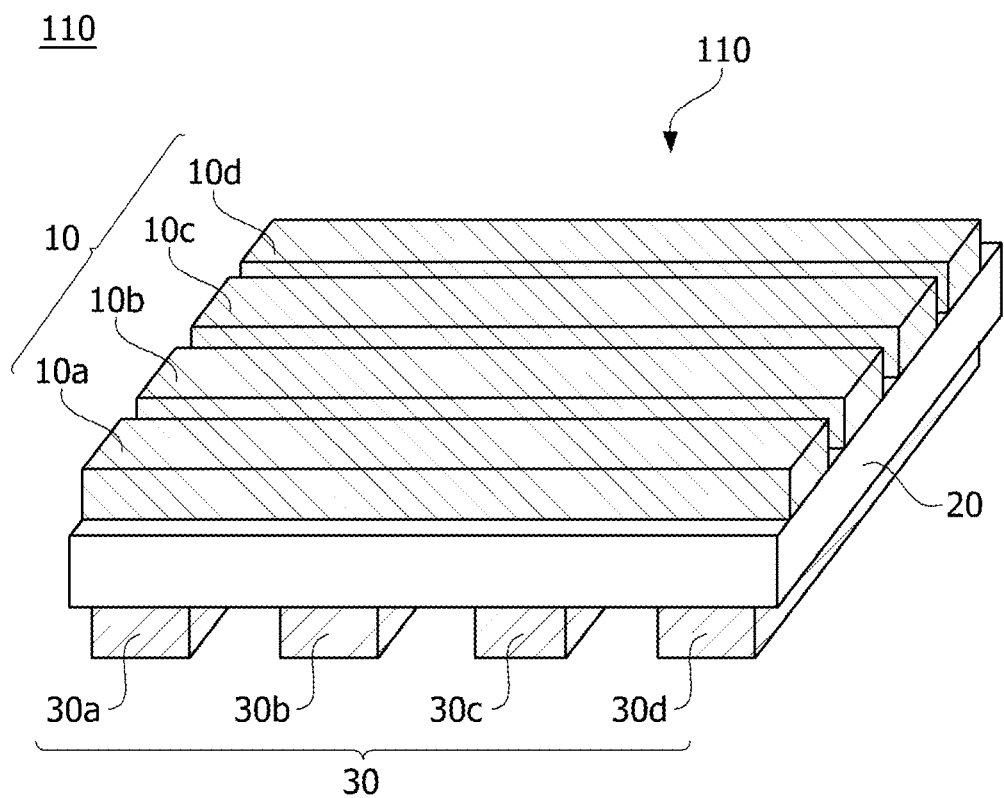
FIG. 3 is a perspective view of a sensor unit of FIG. 2A.

FIG. 3 is a perspective view of the sensor unit of FIG. 2A.

As shown in FIG. 3, when a pressure is applied from the outside to the sensor unit 110, a thickness of the dielectric layer 20 in a region in which the pressure is applied is changed. Although four first electrode patterns 10a, 10b, 10c, and 10d and four second electrode patterns 30a, 30b, 30c, and 30d are shown in the drawing, the number of the first electrode patterns 10a, 10b, 10c, and 10d and the number of the second electrode patterns 30a, 30b, 30c, and 30d are not limited thereto.

The dielectric layer 20 is formed of a material having elasticity. The dielectric layer 20 may further include a conductive filler, but the present invention is not limited thereto. The above dielectric layer 20 may be selected from the group consisting of polyurethane, silicone, and a thermoplastic elastomer, and the conductive filler may be selected from the group consisting of carbon, a metal, ceramic, and a conductive polymer.

When a pressure is applied to the sensor unit 110, a distance between the first electrode layer 10 and the second electrode layer 30 at a point at which the pressure is applied is reduced. In this case, a degree of decrease in a thickness of the dielectric layer 20 between the first electrode layer 10 and the second electrode layer 30 varies according to the applied force. Therefore, the sensor unit 110 according to the embodiment of the present invention may sense the pressure according to a degree of a change in the thickness of the dielectric layer 20.

The first electrode layer 10 and the second electrode layer 30 described above may include a metal having conductivity. Alternatively, the first and second electrode layers 10 and 30 may include fibers having conductivity, or may be formed by printing a conductive ink on the dielectric layer 20. As described above, when the first and second electrode layers 10 and 30 include fibers having conductivity or a conductive ink, the sensor unit 110 may be a fabric type mat having flexibility and elasticity.

Specifically, in the sensor unit 110, the first electrode patterns 10a and 10b are bent by an external pressure, and thus a problem in that the adjacent first electrode patterns 10a and 10b may be in contact with each other may occur. Therefore, a distance a (in FIG. 2A) between the adjacent first electrode patterns 10a and 10b may be 5 mm or more.

When the distance a between the adjacent first electrode patterns 10a and 10b is very wide, a sufficient number of first electrode patterns 10a, 10b, 10c, and 10d may not be formed in the sensor unit 110, so that a facing area may not be sensed. Therefore, the distance a between the adjacent first electrode patterns 10a and 10b may be 30 mm or less, and the distance a between the adjacent first electrode patterns 10a and 10b is not limited thereto. In the same manner, a distance b (in FIG. 2B) between the second electrode patterns 30a and 30b may also range from 5 mm to 30 mm, and the distance b between the adjacent second electrode patterns 30a and 30b is not limited thereto.

In order to accurately measure a change in the thickness of the dielectric layer 20, an area c (in FIG. 2A) of a region in which the first electrode patterns 10a, 10b, 10c, and 10d and the second electrode patterns 30a, 30b, 30c, and 30d overlap each other with the dielectric layer 20 interposed therebetween is preferably 1 cm$^2$ or more. A total area of the sensor unit 110 may be adjusted according to an installed area, but the total area is preferably 400 cm$^2$ or less.

Figure 4A:
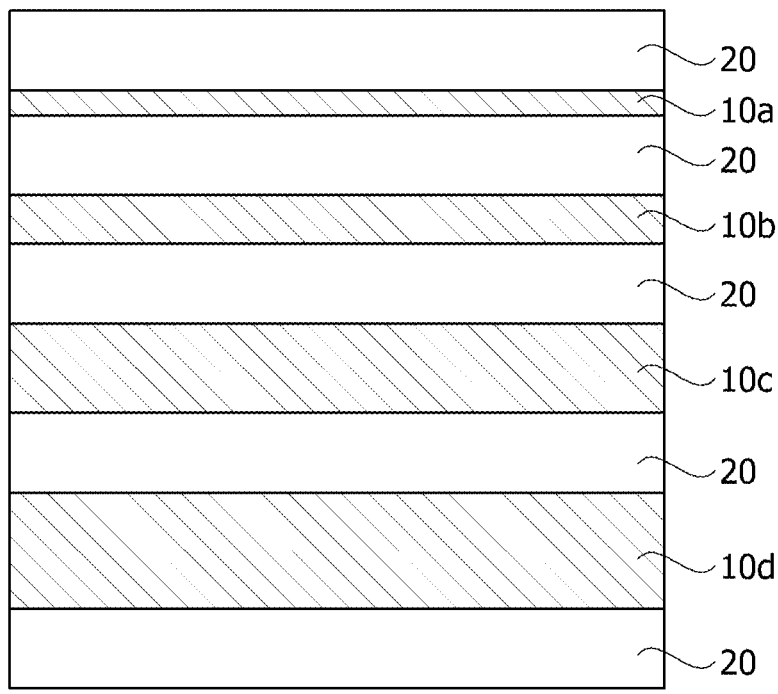
FIGS. 4A to 4C are plan views showing different embodiments of a first electrode pattern.
Figure 4B:
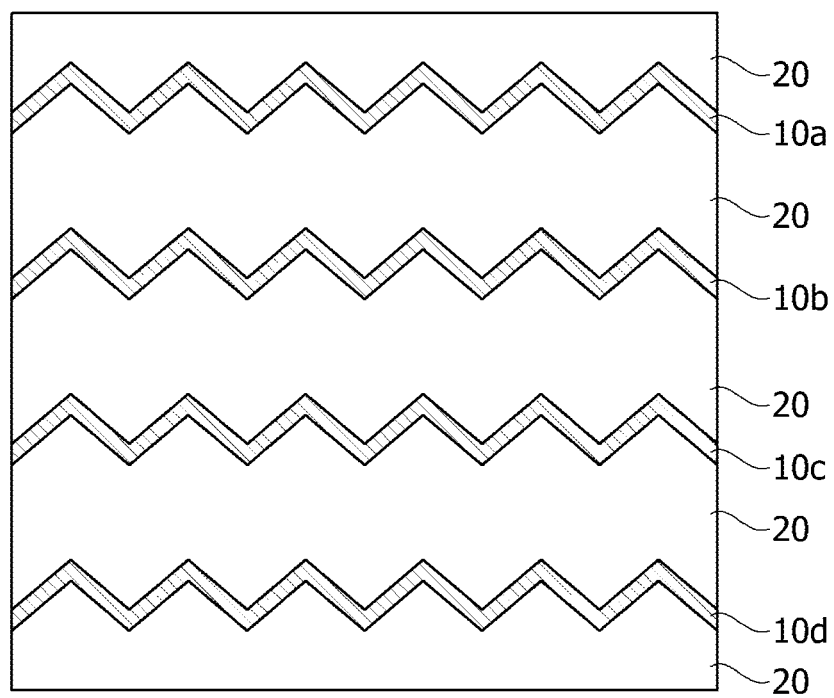
Figure 4C:
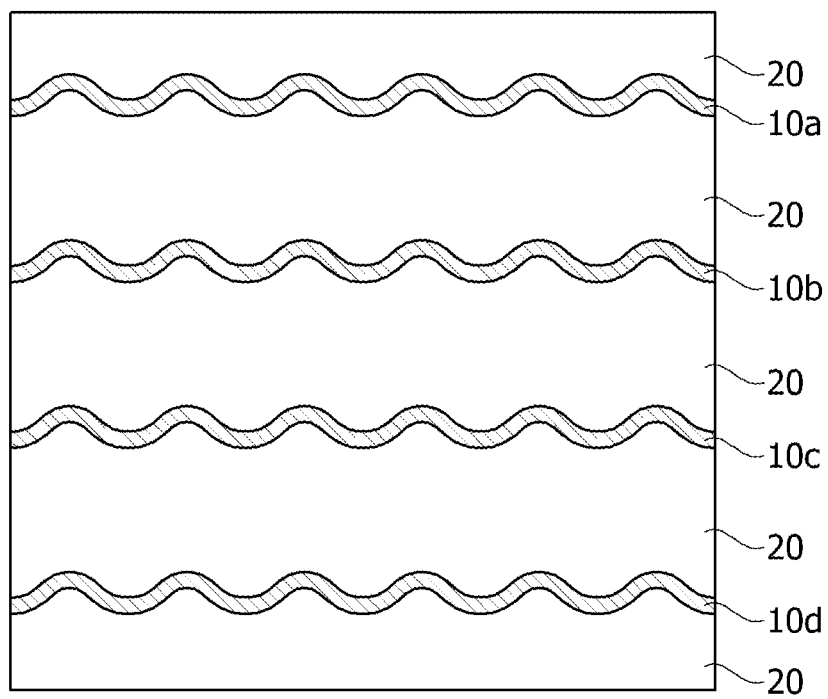

FIGS. 4A to 4C are plan views showing different embodiments of the first electrode patterns.

As shown in FIG. 4A, widths of the first electrode patterns 10a, 10b, 10c, and 10d may not be the same. In this case, all the widths of the first electrode patterns 10a, 10b, 10c, and 10d may be different from each other, or at least some of the widths may be different from each other. Further, the first electrode patterns 10a, 10b, 10c, and 10d may be formed in a zigzag shape as shown in FIG. 4B, or the first electrode patterns 10a, 10b, 10c, and 10d may be in a wavy shape as shown in FIG. 4C. The shapes of the first electrode patterns 10a, 10b, 10c, and 10d are not limited thereto.

Further, although not shown, the plurality of second electrode patterns 30a, 30b, 30c, and 30d which are arranged on the second surface of the dielectric layer 20 in a direction crossing the first electrode patterns 10a, 10b, 10c, and 10d may also be formed to have various shapes like the first electrode patterns 10a, 10b, 10c, and 10d. Specifically, when the first electrode patterns 10a, 10b, 10c, and 10d are formed in a zigzag shape, the second electrode patterns 30a, 30b, 30c, and 30d may be formed to have a wavy shape.

Figure 5:
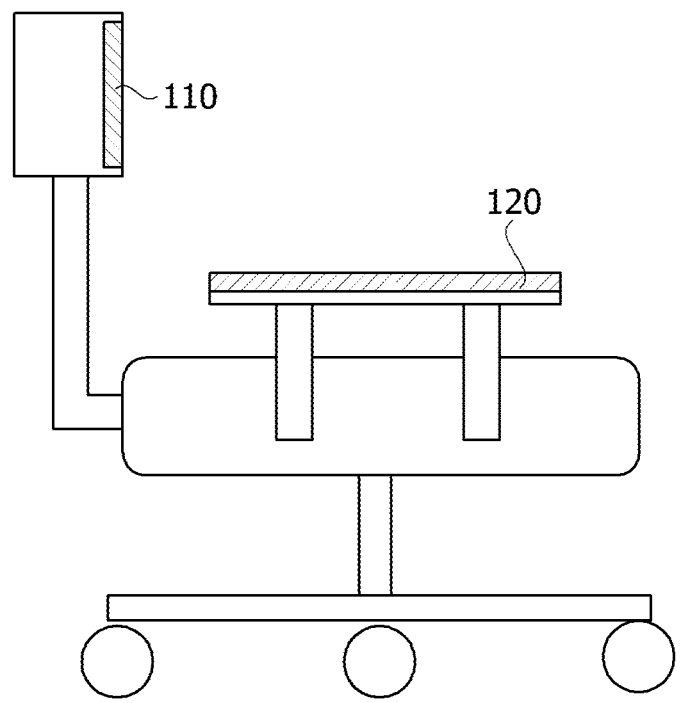
FIG. 5 is a side view of a pressure sensing chair according to another embodiment of the present invention.

FIG. 5 is a side view of a pressure sensing chair according to another embodiment of the present invention.

As shown in FIG. 5, a sensor unit 110 may be disposed in a backrest of the chair. Alternatively, although not shown, the sensor unit 110 may be disposed in both of a seat and a backrest of the chair. In this case, a posture of a person as well as a body pressure and a distribution of the body pressure may be detected. That is, when the sensor unit 110 is disposed in the backrest of the chair, the sensor unit 110 may determine whether the person is sitting in a right posture or sitting in an inclined posture, and obtain posture information of the person through the above-described communication unit 130.

Furthermore, in the case in which the sensor unit 110 is disposed in the backrest, when the pressure is not detected in the sensor unit 110 for a predetermined time, for example, one minute, a module unit 120 may give an alarm about the posture to the person through an alarm unit (not shown).

Figure 6A:
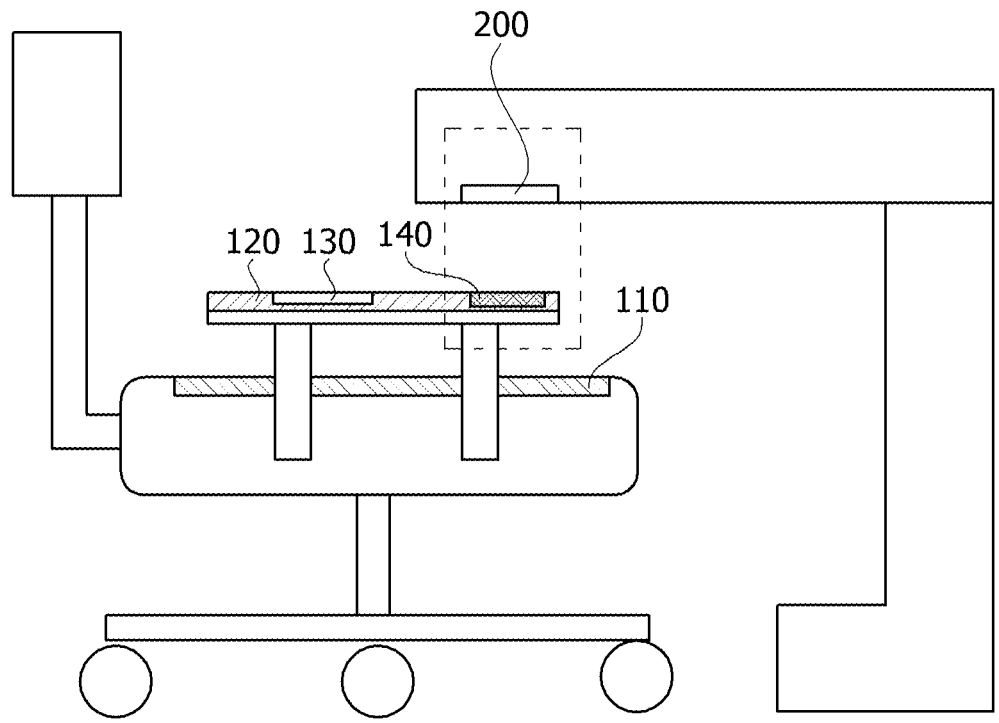
FIG. 6A is a view showing a wireless charging method of FIG. 1.

FIG. 6A is a view showing a wireless charging method of FIG. 1.

As shown in FIG. 6A, a module unit 120 of a pressure sensing chair may be installed in a chair, and most preferably, may be installed in an armrest of the chair. This is for positioning the chair to be adjacent to a wireless power transmission unit 200 disposed in a device such as a desk. That is, a wireless charging unit 140 disposed in the module unit 120 and the wireless power transmission unit 200 may be disposed to be adjacent to each other, so that power may be charged wirelessly.

Particularly, the armrest of the chair and a portion of the desk overlap even when a person is seated in the chair, so that the wireless charging is possible regardless of whether the person is seated. To this end, the wireless charging unit 140 is preferably positioned farther from the backrest of the chair than the communication unit 130.

Figure 6B:
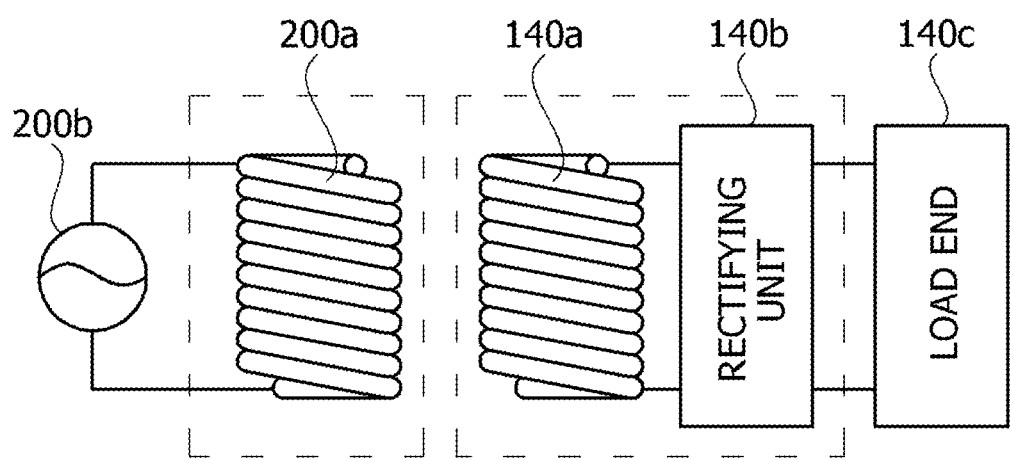
FIG. 6B is a view showing a wireless charging system of FIG. 6A.

FIG. 6B is a view showing a wireless charging system of FIG. 6A.

As shown in FIG. 6B, the wireless charging system may include a transmission coil 200a, a reception coil 140a, a rectifying unit 140b, a power source 200b, and a load end 140c. In this case, the transmission coil 200a and the power source 200b may be included in the wireless power transmission unit 200, and the reception coil 140a, the rectifying unit 140b, and the load end 140c may be included in the wireless charging unit 140.

The power source 200b may generate an alternating current (AC) power having a predetermined frequency to supply the AC power to the transmission coil 200a of the wireless power transmission unit 200. The AC power generated by the transmission coil 200a may be transmitted to the reception coil 140a inductively coupled to the transmission coil 200a, or power of the transmission coil 200a may be transmitted to the wireless charging unit 140 having the same resonance frequency as that of the wireless power transmission unit 200 by a frequency resonance method.

Power transmitted to the reception coil 140a using an electromagnetic induction method or a resonance method may be rectified through the rectifying unit 140b and transmitted to the load end 140c. In this case, the load end 140c may be a battery or a device in which a battery is embedded, but the present invention is not limited thereto.

That is, in the pressure sensing chair according to the embodiment of the present invention described above, the sensor unit 110 capable of detecting a pressure may be disposed in at least one of the seat and the backrest to detect a pressure distribution and posture information according to seating of the person, and the sensor unit 110 may be formed in the form of a mat to sense the body pressure in a facing area. Further, the first and second electrode layers 10 and 30 of the sensor unit 110 may be formed of fibers having conductivity or may be formed by printing a conductive ink on a surface of the dielectric layer 20, and thus flexibility and elasticity of the sensor unit 110 may be improved.

In addition, since the pressure sensing chair includes the wireless charging unit 140, the pressure sensing chair may be wirelessly charged and an on/off operation of the wireless charging unit 140 may be controlled according to whether a pressure is sensed by the sensor unit 110. Further, since the pressure sensing chair includes the communication unit 130, the pressure distribution and the posture information sensed by the sensor unit 110 may be transmitted to an external device.

While the example embodiments of the present invention and their advantages have been described above in detail, it should be understood that various changes, substitutions and alterations may be made herein without departing from the scope of the present invention as defined by the following claims.

The invention claimed is:

1. A body pressure sensing chair comprising:
a sensor unit disposed at a seat of the chair, the sensor unit to detect a pressure on the seat; and
a module unit electrically connected to the sensor unit and including a communication unit and a wireless charging unit, the module unit being disposed in an armrest,
wherein the sensor unit includes:
a first electrode layer including a plurality of first electrode patterns arranged in a first direction,
a second electrode layer including a plurality of second electrode patterns arranged in a second direction crossing the first direction, and
a dielectric layer arranged between the first electrode layer and the second electrode layer,
the plurality of first electrode patterns include regions which overlap the plurality of second electrode patterns, and
the overlap regions are arranged to be spaced apart from each other.

2. The body pressure sensing chair of claim 1, wherein the sensor unit senses a change in a thickness of the dielectric layer in the regions by an external pressure, wherein in response to the detection of the pressure on the seat by the sensor unit, the wireless charging unit is to be turned on.

3. The body pressure sensing chair of claim 1, wherein the communication unit includes a communication module such as a Bluetooth module, a Z-Wave module, or the like, and the communication unit transmits pressure information sensed by the sensor unit to a receiver.

4. The body pressure sensing chair of claim 1, wherein the wireless charging unit receives wireless power using an electromagnetic induction method or a resonance method.

5. The body pressure sensing chair of claim 1, wherein the first electrode layer and the second electrode layer include fibers having conductivity or are formed by printing a conductive ink on the dielectric layer.

6. The body pressure sensing chair of claim 1, wherein the first electrode patterns and the second electrode patterns have a shape selected from a bar shape, a zigzag shape, and a wavy shape.

7. The body pressure sensing chair of claim 1, wherein widths of the plurality of first electrode patterns are the same as widths of the plurality of second electrode patterns.

8. The body pressure sensing chair of claim 1, wherein at least some of the plurality of first electrode patterns and the plurality of second electrode patterns have different widths.

9. The body pressure sensing chair of claim 1, wherein the module unit further includes an alarm unit configured to output a signal of a posture correction.

10. The body pressure sensing chair of claim 1, wherein the overlap regions are in a form of a matrix.

11. The body pressure sensing chair of claim 1, wherein the sensor unit is in a form of a mat.

12. The body pressure sensing chair of claim 1, wherein:
the plurality of first electrode patterns are arranged to be spaced apart from each other in the first direction; and
the plurality of second electrode patterns are arranged to be spaced apart from each other in the second direction.

13. The body pressure sensing chair of claim 1, wherein, when a pressure is applied to the sensor unit, a distance between the first electrode layer and the second electrode layer in overlap regions decreases.

14. The body pressure sensing chair of claim 1, wherein the dielectric layer includes at least one of polyurethane, silicone, or a thermoplastic elastomer.

15. The body pressure sensing chair of claim 1, wherein:
the dielectric layer includes a conductive filler; and
the conductive filler includes at least one of carbon, a metal, ceramic, and a conductive polymer.

16. The body pressure sensing chair of claim 1, wherein a distance from a backrest of the chair to the wireless charging unit is greater than a distance from the backrest to the communication unit.

17. The body pressure sensing chair of claim 1, wherein distances between the plurality of first electrode patterns range from 5 mm to 30 mm.

18. A sensing system comprising:
a body pressure sensing chair; and
a desk including a power transmission unit configured to transmit power to the body pressure sensing chair,
wherein the body pressure sensing chair includes:
a sensor unit, and
a module unit electrically connected to the sensor unit and including a communication unit and a wireless charging unit,
the sensor unit includes:
a first electrode layer including a plurality of first electrode patterns arranged in a first direction,
a second electrode layer including a plurality of second electrode patterns arranged in a second direction crossing the first direction, and
a dielectric layer arranged between the first electrode layer and the second electrode layer,
the plurality of first electrode patterns include regions which overlap the plurality of second electrode patterns,
the overlap regions are arranged to be spaced apart from each other, and
the power transmission unit transmits power to the wireless charging unit.

* * * * *